United States Patent [19]

Hara et al.

[11] Patent Number: 5,225,572

[45] Date of Patent: Jul. 6, 1993

[54] PROCESS FOR PRODUCING PYROMELLITIC DIANHYDRIDE

[75] Inventors: Tadanori Hara; Noboru Daito, both of Kitakyushu; Masakazu Takeuchi, Yukuhashi; Kunio Wada, Fukuoka, all of Japan

[73] Assignee: Nippon Steel Chemical Co., Ltd., Tokyo, Japan

[21] Appl. No.: 543,518

[22] Filed: Jun. 26, 1990

[30] Foreign Application Priority Data

| Jun. 27, 1989 | [JP] | Japan | 1-164597 |
| Jun. 28, 1989 | [JP] | Japan | 1-163821 |
| Jun. 29, 1989 | [JP] | Japan | 1-165185 |
| Mar. 30, 1990 | [JP] | Japan | 2-81283 |
| Mar. 30, 1990 | [JP] | Japan | 2-81284 |
| Mar. 30, 1990 | [JP] | Japan | 2-81285 |
| Mar. 30, 1990 | [JP] | Japan | 2-81286 |

[51] Int. Cl.$^5$ .................................... C07D 493/04
[52] U.S. Cl. .................................................. 549/239
[58] Field of Search ......................................... 549/239

[56] References Cited

U.S. PATENT DOCUMENTS

| 3,769,360 | 10/1973 | Harper | 260/672 |
| 3,848,012 | 11/1974 | Applegath | 260/671 |
| 3,925,425 | 12/1975 | Draguez de Hault | 260/346.4 |
| 4,185,040 | 1/1980 | Ward | 585/467 |
| 4,665,200 | 5/1987 | Nakanishi et al. | 549/239 |

FOREIGN PATENT DOCUMENTS

| 21600 | 1/1981 | European Pat. Off. . |
| 0021600 | 1/1981 | European Pat. Off. . |
| 0137757 | 4/1985 | European Pat. Off. . |
| 0163231 | 12/1985 | European Pat. Off. . |

OTHER PUBLICATIONS

Fessenden et al., "Organic Chemistry," second ed. pp. 474-483 (1982).
Ault, "Techniques and Experiments for Organic Chemistry, 4th ed." Allyn & Bacon (1983) pp. 62-85.
"Advanced Organic Chemistry, 3rd ed." Jerry Mar. (1985) pp. 479-484.
Chemical Abstracts, vol. 75 97929u (1971).

*Primary Examiner*—Mark L. Bereh
*Assistant Examiner*—Matthew V. Grumbling
*Attorney, Agent, or Firm*—Armstrong, Westermen, Hattori, McLeland & Naughton

[57] ABSTRACT

Pyromellitic dianhydride, useful as raw material for the manufacture of polyimides, is prepared in high yield and purity by the reaction of benzene derivatives such as ethylbenzene, diethylbenzenes, and triethylbenzenes with an ethylating agent in the presence of a Friedel-Crafts catalyst, the separation of tetraethylbenzenes from the reaction products by distillation, the separation of 1,2,4,5-tetraethylbenzene from other tetraethyl benzenes by differential centrifugal precipitation at −10 to −30 degrees Celsius, and the catalytic vapor-phase oxidation of tetraethyl benzenes, using a catalyst containing vanadium pentoxide and titanium dioxide.

4 Claims, No Drawings mainly of diethylbenzenes and triethylbenzenes, preferably of triethylbenzenes.

The ethylating agents useful for this invention include ethylene, halogenated ethanes, and ethanol. Ethylene is preferable.

The reaction of the benzene derivatives with the ethylating agent is carried out in a system containing a Friedel-Crafts catalyst or a solid acid catalyst. The Friedel-Crafts catalysts include common alkylation catalysts such as aluminum chloride and boron trifluoride and the solid acid catalysts include as zeolites and silica-alumina, etc. Zeolites are preferable and they may be Y, X, mordenite, or ZSM-5, either of H-type, modified with metal ions, or modified in the silica to alumina ratio.

The reaction system may contain a solvent if necessary and tolerates the presence of pentaethylbenzene and hexaethylbenzene, but it must be excluded from compounds whose boiling point is close to that of tetraethylbenzene. As will be referred to later, it is allowable to recycle to this reaction system the compounds remaining after the separation of tetraethylbenzene from the reaction products by distillation, for example, ethylbenzene, triethylbenzenes, pentaethylbenzene, and hexaethylbenzene or to recycle 1,2,3,5-tetraethylbenzene that is worthless for the production of pyromellitic dianhydride.

The ethylation is desirably carried out until 3.0 to 5.0 moles, preferably 3.5 to 4.8 moles, of ethyl groups are introduced into 1 mole of a benzene ring. The production of tetraethylbenzenes decreases outside this range of the mole ratio. Moreover, a control of the mole ratio of triethylbenzenes to pentaethylbenzene at roughly unity in the reaction products not only maximizes the production of tetraethylbenzenes but also helps to effect the transalkylation of triethylbenzenes and pentaethylbenzene for additional production of tetraethylbenzenes.

The amount of the Friedel-Crafts catalyst varies with the kind of catalyst, the feed, and the like. A zeolite catalyst is used in an amount of 1 to 25% by weight of the aforesaid ethylated benzenes in a batch system or at a liquid hourly space velocity (LHSV) in the range from 0.1 to 20/hr in a continuous system. The reaction temperature likewise varies with other conditions but it is from 100° to 300° C. In the cases where ethylene is used as an ethylating agent, application of a pressure of 3 to 20 kg/cm$^2$ (gauge) causes the reaction to proceed quantitatively and also enables a control of the ratio of triethylbenzenes to pentaethylbenzene at roughly 1 to 1. With aluminum chloride as a catalyst, the amount is 5 to 25% by weight and the reaction temperature is 70° to 150° C.

It is desirable to stop the addition of the ethylating agent and allow a rearrangement reaction to occur as soon as the ethylation proceeded to a given mole ratio of ethyl group to benzene ring. The reaction products immediately after completion of the ethylation are a mixture of tetraethylbenzenes, triethylbenzenes, diethylbenzenes, pentaethylbenzene, and so forth, with the tetraethylbenzenes forming a relatively small proportion. The rearrangement reaction, however, increases the proportion of tetraethylbenzenes. The transfer of ethyl groups probably occurs between polyethylbenzenes with three or less ethyl groups and those with five or more, resulting in an increased proportion of tetraethylbenzenes. The word "rearrangement reaction" is used here for a transalkylation reaction or for both a transalkylation reaction and an isomerization reaction.

The rearrangement reaction is effected in the presence of a Friedel-Crafts catalyst, preferably aluminum chloride or zeolite. In a batch operation, this reaction can be carried out in the ethylation reactor with fresh addition of the catalyst or in another reactor. In a continuous operation, the reaction is carried out in another reactor installed next to the ethylation reactor. It is allowable here to apply the same reaction conditions as those for the ethylation with respect to temperature, agitation, and the like. In the case of a zeolite catalyst, however, it is recommended to set the temperature lower than that for the ethylation by 50° to 100° C. in order to suppress the decomposition reaction and to set the pressure near the atmospheric pressure. The proportion of tetraethylbenzenes will reach 50 to 85% by weight when the mole ratio of ethyl group to benzene ring is brought into the aforesaid desirable range and the rearrangement reaction is carried out sufficiently.

The reaction products are separated from the catalyst in the usual manner and then distilled to separate tetraethylbenzenes from other ethylated benzenes. Such other ethylated benzenes comprise lower-boiling fractions of ethylbenzene, diethylbenzenes, triethylbenzenes, etc. and higher-boiling fractions of pentaethylbenzene, etc. The reaction products additionally contain low-boiling by-products such as benzene and high-boiling by-products such as polymers and these by-products can be separated easily by distillation.

It is desirable to return at least a portion of the other ethylated benzenes to the ethylation reaction system or to the rearrangement reaction system. In the cases where a higher-boiling pentaethylbenzene fraction and a lower-boiling triethylbenzene fraction are present at a roughly equimolar ratio, they may be submitted to transalkylation in a reactor separate from the one for the aforesaid rearrangement reaction. Preferably, the fractions of diethylbenzenes and triethylbenzenes are returned in whole. More preferably, the fractions of diethylbenzenes and triethylbenzenes in whole and those of pentaethylbenzene and hexaethylbenzene in whole are returned. In this case, it is desirable to return the fractions of pentaethylbenzene and hexaethylbenzene and a corresponding quantity of triethylbenzenes or diethylbenzenes (that is, a quantity to bring the mole ratio of the total ethyl groups to benzene rings to 4) not to the ethylation reaction system but to the rearrangement reaction system. The rearrangement reaction system here may be the one for the rearrangement reaction of either the reaction products from the ethylation themselves or of the higher-boiling fractions of pentaethylbenzene, etc. and the lower-boiling fractions of triethylbenzenes, etc. obtained by fractional distillation of said reaction products, the latter system being preferable.

Of the fractions other than that of tetraethylbenzenes obtained by fractional distillation of the reaction products from the ethylation, the lower-boiling diethylbenzene and triethylbenzene fractions and the higher-boiling pentaethylbenzene and hexaethylbenzene fractions are returned to one or the other of the reaction systems for eventual conversion to tetraethylbenzenes, thus enhancing the yield of tetraethylbenzenes. In particular, it is possible to obtain tetraethylbenzenes in a yield of 90% or more by returning the whole fractions other than those for the aforesaid polymers and decomposition products, namely the fractions of benzene, ethylbenzene, diethylbenzenes, triethylbenzenes, pentaethylbenzene, and hexaethylbenzene.

PROCESS FOR PRODUCING PYROMELLITIC DIANHYDRIDE

FIELD OF THE INVENTION AND RELATED ART STATEMENT

This invention relates to a process for producing pyromellitic dianhydride, which is useful as raw material for the manufacture of polyimides.

The catalytic vapor-phase oxidation of a tetraalkylbenzene such as durene is known to yield pyromellitic dianhydride as described in U.S. Pat. No. 4,665,200 and Eur. Pat. Appl. EP 163231. A concrete example is given in U.S. Pat. No. 3,925,425 for the catalytic vapor-phase oxidation of tetraethylbenzene to pyromellitic dianhydride. The patent, however, makes no mention of a practical process for producing the feed tetraethylbenzene and refers to a low yield of pyromellitic dianhydride, 58.2% by weight based on the tetraethylbenzene.

Tetraethylbenzene is produced by ethylating benzene with an ethylating agent such as ethylene, but no report has been published on processes suitable for the commercial production of this compound. The alkylation of benzene proceeds in the presence of a Friedel-Crafts catalyst, but it is far more difficult to produce selectively tetraethylbenzene that has four ethyl groups than ethylbenzene that has a single ethyl group.

Ethylbenzene is produced in large quantities as raw material for styrene together with by-product polyethylbenzenes which mainly consist of diethylbenzenes and the polyethylbenzenes are recycled to the transalkylation step or discharged as residual oil and the like as described in U.S. Pat. No. 3,848,012.

The use of zeolite as a Friedel-Crafts catalyst in the production of alkylbenzenes is described in U.S. Pat. No. 4,185,040, EP 21600, and EP 137757. Zeolite is also used as a catalyst for the transalkylation of diethylbenzenes and benzene to produce ethylbenzene as disclosed in U.S. Pat. No. 3,769,360. Moreover, the production of polyethylbenzenes with the use of Friedel-Crafts catalysts is known in Chem. Abstr. Vol. 75, 97929u (1971).

The methylation of benzene presents a greater difficulty than other alkylations and this makes it difficult to produce durene in large quantities at low cost by a synthetic route. The ethylation, or isopropylation, of benzene is easier to carry out than the methylation, but it yields two isomeric tetraethylbenzenes accompanied by large quantities of by-products such as di-, tri-, and penta-substitution products, thus making it extremely difficult to produce 1,2,4,5-tetraethylbenzene in high yields. Furthermore, the oxidation of durene to pyromellitic dianhydride is relatively easy but that of tetraethylbenzene is rather difficult for the reason that the conversion of the methyl group to carboxyl group requires no loss of carbon atom whereas that of the ethyl group must lose one carbon atom in the form of carbon dioxide or four carbon atoms for each benzene ring with the carbon atoms located in the benzene ring showing a tendency to become involved in the oxidation. Furthermore, the other tetraethylbenzene isomer or 1,2,3,5-tetraethylbenzene would not give pyromellitic dianhydride when oxidized.

For the reasons mentioned above, the production of pyromellitic dianhydride from tetraethylbenzene has not been practiced on an industrial scale.

OBJECT AND SUMMARY OF THE INVENTION

It is an object of this invention to provide a process for producing pyromellitic dianhydride selectively in high yields from tetraethylbenzene starting with benzene derivatives.

Another object of this invention is to provide a process for utilizing the by-products obtained in the production of ethylbenzene.

A further object of this invention is to provide a process for producing pyromellitic dianhydride selectively in high yields by the reaction of benzene derivatives with an ethylating agent in the presence of a Friedel-Crafts catalyst followed by the catalytic vapor-phase oxidation of the resulting tetraethylbenzene with the use of a catalyst containing vanadium pentoxide and titanium dioxide as active ingredients.

This invention relates to a process for producing pyromellitic dianhydride which comprises allowing one or two or more benzene derivatives selected from a group of benzene, ethylbenzene, diethylbenzenes, and triethylbenzenes to react with an ethylating agent in the presence of a Friedel-Crafts catalyst, separating tetraethylbenzene from the reaction products by distillation, and oxidizing the tetraethylbenzene in the vapor phase in the presence of a catalyst containing vanadium pentoxide and titanium dioxide as active ingredients.

In the process of this invention, tetraethylbenzene is prepared first and then converted to pyromellitic dianhydride by the catalytic vapor-phase oxidation. The tetraethylbenzene here is prepared as follows.

The feed is one or a mixture of two or more benzene derivatives selected from a group of benzene, ethylbenzene, diethylbenzenes, and triethylbenzenes, preferably mainly consisting of diethylbenzenes and/or triethylbenzenes, more preferably mainly consisting of triethylbenzenes. Here, "mainly consisting" means 70% by weight or more, preferably 80% by weight or more. A benzene derivative of particular choice is polyethylbenzenes occurring as by-products in the production of ethylbenzene from benzene and ethylene in the presence of a Friedel-Crafts catalyst.

Ethylbenzene is produced in large quantities by the reaction of benzene with ethylene in the presence of a Friedel-Crafts catalyst such as aluminum chloride and zeolite. The reaction products are distilled to furnish a benzene fraction, an ethylbenzene fraction, a polyethylbenzene fraction, and the like and the benzene fraction is recycled to the reaction system while the ethylbenzene fraction is recovered as product and the polyethylbenzene fraction is used in the transalkylation reaction with benzene or withdrawn as fuel. In the process of this invention, such polyethylbenzene fraction can be used in part or in whole as a feed for the production of tetraethylbenzene. Polyethylbenzenes occur in an amount of several percent at most since they are by-products in the production of ethylbenzene; however, large-volume production of ethylbenzene often makes a sufficiently large amount of these by-products available for the production of tetraethylbenzene. In case of a shortage of such polyethylbenzenes, the manufacturing conditions for ethylbenzene may be varied to favor an increased production of the polyethylbenzenes, for example, by enhancing the mole ratio of ethylene to benzene, increasing the amount of the catalyst, raising the reaction temperature, or employing zeolite as a catalyst. It is desirable for the polyethylbenzenes to consist Tetraethylbenzenes can be separated easily from other ethylated benzenes by distillation and it is desirable here to raise the concentration of tetraethylbenzenes in the fraction in question to 90% by weight or more by controlling the distillation conditions, for instance, the number of plate of the column. It is, however, not possible to separate 1,2,3,5-tetraethylbenzene from 1,2,4,5-tetraethylbenzene because of extreme closeness of their boiling points and the two are present at an approximate ratio of 4 to 6.

This tetraethylbenzene fraction may be submitted to the catalytic vapor-phase oxidation as a mixture of the isomers or after concentrating one of the isomers, 1,2,4,5-tetraethylbenzene. In the catalytic vapor-phase oxidation of the mixture, 1,2,4,5-tetraethylbenzene yields pyromellitic dianhydride whereas 1,2,3,5-tetraethylbenzene is oxidized entirely to carbon dioxide and carbon monoxide and produces no ill effect in the subsequent purification of pyromellitic dianhydride. This process of using the mixture as a feed has a merit on an industrial scale as it does not require the installation of equipment for the separation of the isomers, but it has a demerit of a lower product yield. As a consequence, it is desirable to separate the isomers if an efficient process is available.

Crystallization, superfractionation, adsorption, and the like, preferably crystallization, are applicable to the separation of the isomers present in the tetraethylbenzene fraction. Crystallization can be effected by varying either the pressure (pressure crystallization) or the temperature (cooling crystallization), the latter being advantageous for its simplicity.

Pressure crystallization is disclosed in Japan Tokkyo Kokai Koho Nos. 58-10, 121 (1983) and 60-48,205 (1985). According to this process, a solution of two or more compounds is pressurized to cause a specified compound to solidify by the action of the pressure and the resulting solid phase is separated from the liquid phase. The solid phase is then placed isothermally under decreasing pressure whereby perspiration occurs and impurities separate out in the liquid phase. The condition essential for the pressure crystallization of 1,2,4,5-tetraethylbenzene is one that turns this isomer solid while keeping the other isomer liquid. A preferable mode of operation is to increase the pressure, isothermally at −15° to 40° C., to 1,000 to 4,000 kgf/cm$^2$ where the solid phase appears and then lower it isothermally to 1,000 to 2,000 kgf/cm$^2$ where the liquid phase is separated from the solid phase by filtration and discharged from the system. 1,2,4,5-Tetraethylbenzene remains solid at this point, but it turns liquid on further reduction of the pressure and is recovered as solid or liquid at the aforesaid temperature.

Cooling crystallization is well known as a process for the purification of materials, but its success depends on the properties of the crystals to be separated. Tetraethylbenzenes are known to crystallize in paste, which has led one to anticipate extreme difficulties in the liquid-solid separation of tetraethylbenzenes and to regard the application of cooling crystallization an impossibility. It has been found, however, that the liquid-solid separation can be attained readily with high purity of crystals by cooling the tetraethylbenzene fraction down to −5° C. or less and subjecting the separated crystals to centrifugation under 500 G or more. Cooling crystallization can be practiced by any process which provides cooling to attain a temperature where one of the isomers remains liquid and the other solid. A preferable mode of operation is to cool the tetraethylbenzene fraction to −5° C. or less, preferably −10° to −30° C., to crystallize 1,2,4,5-tetraethylbenzene and separate the crystals under application of a centrifugal force of 500 G or more, preferably 600 G or more, more preferably 700 G or more. A higher cooling temperature results in a lower yield while a too low cooling temperature causes a loss in purity. For example, cooling to −10° C. can realize a purity of 90% or more while cooling to −25° C. furnishes a purity of 80% or so. A too small centrifugal force cannot effect the liquid-solid separation satisfactorily, thus making no improvement in purity. A crystal recovery rate of 50% or so gives 1,2,4,5-tetraethylbenzene with a purity of 90% or so. The practical purity of 1,2,4,5-tetraethylbenzene is 80 to 95% since a higher purity, although more advantageous for the oxidation reaction, lowers the recovery rate.

1,2,3,5-Tetraethylbenzene after the separation contains a small amount of 1,2,4,5-tetraethylbenzene and besides it can be isomerized readily to 1,2,4,5-tetraethylbenzene. It is therefore desirable to return 1,2,3,5-tetraethylbenzene thus separated to an isomerization reaction or the aforesaid ethylation reaction or rearrangement reaction for the isomerization. The conditions therefor may be identical with those for the ethylation or rearrangement reaction and it is desirable to carry out the isomerization until the isomer ratio reaches an equilibrium. Repetition of this procedure can raise the yield of 1,2,4,5-tetraethylbenzene to 90% or more.

The tetrathylbenzene fraction or 1,2,4,5-tetraethylbenzene after the isomer separation is catalytically oxidized in the vapor phase to pyromellitic dianhydride. The catalyst for this oxidation contains titanium dioxide and vanadium pentoxide as active ingredients. It is composed of an inert support coated with the active ingredients containing preferably 60 to 95% by weight, advantageously 70 to 90% by weight, of titanium dioxide and 5–40% by weight, advantageously 10 to 30% by weight, of vanadium pentoxide. The raw materials for titanium dioxide include anatase-type titanium dioxide and titanium dioxide hydrate while those for vanadium pentoxide include compounds that are convertible to vanadium pentoxide by heating, for example, ammonium vanadate and vanadyl sulfate. Besides these, a small amount of other active ingredients such as K, Na, Rb, Cs, Mo, W, Cr, Sn, P, Zr, Fe, Nb, Sb, Bi and B may be added in the form of their water-soluble compounds. Such other ingredients are added in an amount of 10% by weight or less, preferably 5% by weight or less on the basis of the active ingredients, and they exist as oxide or sulfate etc. The specific name of a compound such as vanadium pentoxide is used here for the convenience of calculation and the element in question may be present in the catalyst in another oxidation state or as another compound. The inert supports include nonporous silicates, porcelain, silicon carbide, and steatite. Such supports are spherical, cylindrical, or annular in shape with a diameter of 3 to 12 mm, preferably 6 to 10 mm. The amount of the active catalyst ingredients on the support is desirably 40 to 150 g per 1 liter of the support.

The catalytic vapor-phase oxidation of tetraethylbenzenes is carried out in a reactor packed with the aforesaid catalyst using a gas containing molecular oxygen. In this case, two kinds of catalysts may be prepared and packed in two layers in the reactor. The reaction conditions are: temperature, 330° to 450° C.; concentration of tetraethylbenzenes, 20 to 70 g/Nm$^3$ of air; gas hourly space velocity (GHSV), 1,000 to 10,000/hr. The purity of pyromellitic anhydride is improved by using air diluted with nitrogen, carbon dioxide, or the like to an oxygen concentration of 7 to 20% by volume as an oxygen-containing gas. Moreover, the purity of pyromellitic anhydride is improved by raising a reaction temperature. For example, even if 1,2,4,5-tetraethylbenzene having a purity of about 50% is used as a raw material, a purity of pyromellitic anhydride may be improved up to about 90 wt % by raising a reaction temperature. However, a yield of pyromellitic anhydride may decrease when a reaction temperature is too high.

The process of this invention gives pyromellitic dianhydride in high purity and yield.

DETAILED DESCRIPTION OF THE PREFERRED EMBODIMENT

Examples of this invention will be given below. The percentage and parts in the examples are by weight.

EXAMPLE 1

In a reactor fitted with a stirrer and a reflux condenser were placed aluminum chloride and 250 g of the polyethylbenzene fraction (containing 91% of diethylbenzenes, 7% of triethylbenzenes, and 2% of others) obtained as by-product in the manufacture of ethylbenzene by the alkylation of benzene with ethylene in the presence of 25 g of aluminum chloride, the mixture was heated, and ethylene was supplied to the mixture at a given rate to effect the ethylation.

Upon completion of the ethylation, the supply of ethylene was stopped and the mixture was kept stirred at the same temperature to effect the rearrangement reaction until the composition of the reaction products became constant. The reaction mixture was cooled, freed from the catalyst, and distilled to recover a tetraethylbenzene fraction (containing 59.2% of 1,2,4,5-tetraethylbenzene, 39.6% of 1,2,3,5-tetraethylbenzene, and 0.4% of triethylbenzenes). On the other hand, a diethylbenzene fraction, a triethylbenzene fraction, and a pentaethylbenzene fraction were returned in part as a recycle fraction to the aforesaid reactor for the second reaction and the ethylation and the rearrangement reaction were carried out.

A portion of the tetraethylbenzene fraction was introduced into a stainless steel vessel and cooled by dry ice with stirring to a given temperature to cause crystals to separate. The slurry obtained was charged to a centrifuge and rotated under 750 G for 2 minutes to perform the liquid-solid separation. Cotton cloth of 300 mesh was used as a filter. The condition and the results are shown in Table 1.

TABLE 1

| Feed No. | Cooling temperature °C. | Solid phase Purity % | Solid phase Proportion % | Liquid phase Concentration % | Liquid phase Proportion % |
|---|---|---|---|---|---|
| 1 | −14.0 | 91.1 | 25.6 | 49.7 | 74.4 |
| 2 | −19.5 | 87.9 | 39.3 | 42.3 | 60.7 |
| 3 | −22.5 | 87.0 | 64.1 | 39.4 | 55.2 |
| 4 | −26.8 | 80.9 | 73.4 | 35.1 | 45.1 |

(Note) The purity of the solid phase denotes that of 1,2,4,5-tetraethylbenzene, the concentration of the liquid phase denotes that of 1,2,4,5-tetraethylbenzene, and the proportion denotes that of the solid or liquid phase.

Separately, a portion of the aforesaid tetraethylbenzene fraction was introduced into a pressure vessel provided with a filtering function, kept at 0° C. in a constant-temperature bath, and pressurized isothermally to 4,000 kgf/cm² to separate the solid phase. This condition was maintained for 30 minutes, the pressure was then lowered to 2,000 kgf/cm², the compression filtration of the contents was started slowly from there, and the liquid phase was discharged from the system. The solid phase (Feed No. 5) was 98.6% in purity and recovered at a rate of 39.1%.

Next, powdered titanium dioxide, ammonium metavanadate, and a small amount of other active catalyst ingredients were added to deionized water and stirred to form a slurry while dissolving any water-soluble compounds. Ring-shaped porcelain supports, 8 mm in diameter and 6 mm in height, were preheated at 200° to 250° C. in a rotating oven and the aforesaid slurry was sprayed on the rotating supports such as to deposit 80 g of the catalyst ingredients on 1 liter of the supports to furnish a catalyst. The active ingredients of a variety of catalysts thus prepared are shown in Table 2.

TABLE 2

| Catalyst | $V_2O_5$ (%) | $TiO_2$ (%) | Other ingredients (%) | |
|---|---|---|---|---|
| A | 10 | 90 | — | |
| B | 15 | 85 | — | |
| C | 20 | 80 | — | |
| D | 25 | 75 | — | |
| E | 30 | 70 | — | |
| F | 20 | 78.5 | $P_2O_5$ | 1.5 |
| G | 20 | 77 | $P_2O_5$ | 3 |
| H | 20 | 79.5 | $P_2O_5$ | 0.5 |
| I | 20 | 79 | $Rb_2SO_4$ | 1.0 |
| J | 20 | 79.5 | $B_2O_3$ | 0.5 |
| K | 20 | 79 | $B_2O_3$ | 1.0 |
| L | 20 | 79.5 | $MgSO_4$ | 0.5 |
| M | 20 | 79 | $MgSO_4$ | 1.0 |

The solid phases (Feed Nos. 1 to 5) and the tetraethylbenzene fraction obtained above were each submitted to the catalytic vapor-phase oxidation in a reactor, 25 mm in diameter, packed with 1 liter of one of the catalystes prepared above under the conditions: concentration of the feed, 30 g/Nm³ of air; GHSV, 4,000/hr; optimal temperature, 350° to 380° C. The feed, catalyst, and yield of pyromellitic dianhydride are shown in Table 3.

TABLE 3

| Run No. | Catalyst | Feed No. | Yield of pyromellitic dianhydride (mole %) |
|---|---|---|---|
| 1 | A | 5 | 55.6 |
| 2 | B | 5 | 55.1 |
| 3 | C | 5 | 57.3 |
| 4 | D | 5 | 56.5 |
| 5 | E | 5 | 54.2 |
| 6 | F | 5 | 58.5 |
| 7 | G | 5 | 58.0 |
| 8 | H | 5 | 59.0 |
| 9 | I | 5 | 58.3 |
| 10 | C | 0 | 52.3 |
| 11 | F | 1 | 58.5 |
| 12 | F | 2 | 57.7 |
| 13 | F | 3 | 57.7 |
| 14 | F | 4 | 57.2 |
| 15 | J | 3 | 60.5 |
| 16 | K | 3 | 60.1 |
| 17 | L | 3 | 59.8 |
| 18 | M | 3 | 60.2 |

(Note) Feeds Nos. 1 to 4 refer to those in Table 1 and Feed No. 5 to the aforesaid solid phase. Feed No. 0 denotes tha tetraethylbenzene fraction. The yield of pyromellitic dianhydride is expressed as the mole ratio in percentage of pyromellitic dianhydride to 1,2,4,5-tetraethylbenzene in the feed.

Pyromellitic dianhydride thus obtained was 95% or so in purity in each run. The purity showed virtually no change with the kind of feed, but it varied with the reaction temperature. The reaction was carried out on Feed No. 5 in the presence of Catalyst F at different temperatures. The results are shown in Table 4.

TABLE 4

| Run No. | Reaction temperature (°C.) | Pyromellitic dianhydride | |
| --- | --- | --- | --- |
| | | Purity (%) | Yield (mole %) |
| 19 | 370 | 95.0 | 58.5 |
| 20 | 372 | 97.0 | 57.3 |
| 21 | 373 | 98.0 | 56.6 |

EXAMPLE 2

The polyethylbenzene fraction (containing 2% of ethylbenzene, 90% of diethylbenzenes, and 8% of triethylbenzenes) formed as by-product in the manufacture of ethylbenzene by the alkylation of benzene with ethylene in the presence of aluminum chloride was placed in a reactor fitted with a stirrer and a reflux condenser, the fraction was heated, approximately 2.2 times in mole of ethylene was introduced into the fraction in the presence of 5% of anhydrous aluminum chloride, and the mixture was allowed to react at 130° C. for about 6 hours to give a reaction mixture containing roughly 30% of triethylbenzenes, 40% of tetraethylbenzenes, and 30% of pentaethylbenzene. The supply of ethylene was then stopped and the reaction mixture was continuously stirred at the same temperature for 3 hours to effect the rearrangement reaction to give reaction product containing roughly 12% of triethylbenzenes, 76% of tetraethylbenzenes, and 12% of pentaethylbenzene.

The reaction product was taken out, freed from the catalyst, and fractionally distilled to yield a tetraethylbenzene fraction (containing 55% of 1,2,4,5-tetraethylbenzene and 45% of 1,2,3,5-tetraethylbenzene), a triethylbenzene fraction, and a pentaethylbenzene fraction. The triethylbenzene and pentaethylbenzene fractions were sent to the separately provided transalkylation step and they were allowed to react in the presence of 5% of aluminum chloride at 130° C. for 8 hours to give a reaction mixture containing roughly 13% of triethylbenzenes, 75% of tetraethylbenzenes, and 11% of pentaethylbenzene. This was fractionally distilled to yield a triethylbenzene fraction, a tetraethylbenzene fraction, and a pentaethylbenzene fraction with the tetraethylbenzene fraction recovered and the other two fractions returned to the aforesaid transalkylation step.

The both tetraethylbenzene fractions thus obtained were put together, cooled by dry ice and filtered under a centrifugal force of 750 G as in Example 1 to effect the liquid-solid separation and the solid phase with a purity of 85.5% was recovered at a proportion of 44.0%. The liquid phase was returned to the aforesaid transalkylation step. By repetition of this procedure, 85% to 90% of the benzene rings in the polyethylbenzene fraction was utilized to form 1,2,4,5-tetraethylbenzene.

The solid phase mainly consisting of 1,2,4,5-tetraethylbenzene was subjected to the catalytic vapor-phase oxidation using Catalyst F of Example 1. The yield of pyromellitic dianhydride was 58.0 mole %.

EXAMPLE 3

The reaction mixture (containing 14.0% of ethylbenzene, 4.4% of diethylbenzenes, 1.1% of triethylbenzenes, 0.3% of tetraethylbenzenes, and 80% of benzene) obtained by the reaction of benzene with ethylene in the presence of Y zeolite as a catalyst was distilled to give a benzene fraction, an ethylbenzene fraction, a triethylbenzene fraction, a tetraethylbenzene fraction, and a high-boiling fraction. The benzene fraction was returned to the step for the aforesaid reaction with ethylene, the ethylbenzene fraction was recovered as product, the diethylbenzene fraction was sent to a step for the Y zeolite-catalyzed transalkylation with benzene, the triethylbenzene fraction was sent to a step for the preparation of tetraethylbenzenes, and the tetraethylbenzene fraction was recovered as a feed for the preparation of pyromellitic dianhydride.

The triethylbenzene fraction was placed in a reactor fitted with a stirrer and a reflux condenser and heated, approximately 1.2 times in mole of ethylene was introduced in the presence of 15% of Y zeolite, and the mixture was allowed to react at a temperature of 300° C. and a pressure of 20 kg/cm² (gauge) for about 6 hours to yield a reaction mixture containing roughly 8% of triethylbenzenes, 58% of tetraethylbenzenes, 16% of pentaethylbenzene, and 18% of hexaethylbenzene. The supply of ethylene was then stopped and the mixture was continuously stirred at the same temperature and pressure for 5 hours to effect the rearrangement reaction which yielded reaction product containing roughly 27% of triethylbenzenes, 40% of tetraethylbenzenes, and 2% of pentaethylbenzene.

The reaction product was taken out, freed from the catalyst, and distilled to give a tetraethylbenzene fraction (containing 55% of 1,2,4,5-tetraethylbenzene and 45% 1,2,3,5-tetraethylbenzene), a triethylbenzene fraction, and a pentaethylbenzene fraction. The triethylbenzene and pentaethylbenzene fractions were sent to the separate transalkylation step where they were heated at 130° C. for 8 hours in the presence of 5% of aluminum chloride to yield a reaction mixture containing roughly 13% of triethylbenzenes, 75% of tetraethylbenzenes, and 11% of pentaethylbenzene. This was distilled to give a triethylbenzene fraction, a tetraethylbenzene fraction, and a pentaethylbenzene fraction with the tetraethylbenzene fraction recovered and the other two fractions returned to the aforesaid step for the preparation of tetraethylbenzenes. By repeating the procedure, 85 to 90 mole % of the benzene rings in the feed triethylbenzene fraction was converted to 1,2,4,5-tetraethylbenzene.

The both tetraethylbenzene fractions thus obtained were put together, cooled by dry ice and filtered under a centrifugal force of 750 G as in Example 1 to effect the liquid-solid separation and recover the solid phase with a purity of 88.0% at a proportion of 42.2%. The liquid phase was returned to the aforesaid transalkylation step.

The solid phase mainly consisting of 1,2,4,5-tetraethylbenzene was subjected to the catalytic vapor-phase oxidation under the similar conditions using Catalysts F, J, and L of Example 1. The yields of pyromellitic dianhydride were 58.5, 60.1, and 59.3 mole % respectively.

EXAMPLE 4

In a reactor fitted with a stirrer and a reflux condenser were placed 250 g of the triethylbenzene fraction (containing 2.8% of diethylbenzenes and 97% of triethylbenzenes) obtained as by-product in the preparation of ethylbenzene from benzene and ethylene in the presence of aluminum chloride and 50 g of pulverized Y zeolite A or pulverized Y zeolite B, the contents were heated, ethylene was continuously introduced at an ethylene pressure of 10 to 15 kg/cm² (gauge), and the mixture was allowed to react for 0.5 hours at a temperature of 250° or 300° C. in the case of Y zeolite A or 250° C. in the case of Y zeolite B. Thereafter, the mixture was stirred continuously for 4 hour to effect the rearrangement reaction and the reaction mixture was taken out, freed from the catalyst, and distilled to give a tetraethylbenzene fraction, a diethylbenzene fraction, a triethylbenzene fraction, and a pentaethylbenzene fraction. The diethylbenzene, triethylbenzene, and pentaethylbenzene fractions were combined to form a recycle fraction and a portion of it was returned to the aforesaid reactor to carry out the second reaction with sampling and analysis made at regular intervals. The second reaction was carried out as the first one except using a total of 500 g of ethylated benzenes inclusive of 250 g of the recycle fraction, introducing ethylene for ¾ hours, and running the rearrangement reaction for 4 hour. The composition of the reaction products of the first and second reactions are shown respectively in Tables 5 and 6.

TABLE 5

| Composition | Run No. 1 | Run No 2 | Run No. 3 |
| --- | --- | --- | --- |
| Diethylbenzenes | 2.4 | 1.7 | 2.4 |
| 1,3,5-Triethylbenzene | 51.1 | 16.9 | 7.9 |
| 1,2,4-Triethylbenzene | 12.7 | 6.1 | 4.3 |
| 1,2,3,5-Tetraethylbenzene | 9.7 | 18.4 | 15.8 |
| 1,2,4,5-Tetraethylbenzene | 11.4 | 14.6 | 19.1 |
| Pentaethylbenzene | 7.4 | 39.6 | 41.0 |
| Hexaethylbenzene | 0.1 | 0.3 | 4.5 |
| Others | 5.8 | 2.4 | 5.0 |

(Notes)
(1) The composition is based on the ratio of areas in the gas chromatogram.
(2) Run No. 1: Y zeolie A, 300° C.
Run No. 2: Y zeolite B, 250° C.
Run No. 3: Y zeolite C, 250° C.

TABLE 6

| Composition | Run No. 1 final | Run No. 2 After 3 hr | Run No. 2 Final | Run No. 3 After 3 hr | Run No. 3 Final |
| --- | --- | --- | --- | --- | --- |
| Diethylbenzenes | 0.8 | 0.9 | 0.4 | 0.5 | 0.5 |
| 1,3,5-Triethylbenzene | 14.3 | 7.8 | 2.8 | 1.6 | 2.6 |
| 1,2,4-Triethylbenzene | 10.6 | 3.0 | 1.7 | 1.0 | 1.7 |
| 1,2,3,5-Tetraethylbenzene | 21.6 | 19.7 | 23.0 | 20.8 | 24.5 |
| 1,2,4,5-Tetraethylbenzene | 30.7 | 16.8 | 29.1 | 25.9 | 31.4 |
| Pentaethylbenzene | 4.0 | 47.5 | 37.8 | 38.1 | 27.3 |
| Hexaethylbenzene | 0.0 | 0.7 | 1.4 | 4.4 | 1.5 |
| Others | 18.0 | 3.6 | 3.8 | 7.7 | 10.5 |

The final reaction products in Run Nos. 1 to 3 in Table 6 were each distilled to take out a tetraethylbenzene fraction, which was combined with the tetraethylbenzene fraction obtained in the first reaction, cooled by dry ice, filtered under a centrifugal force of 750 G to effect the liquid-solid separation and recover the solid phase as in Example 1. The cooling temperature was varied to vary the purity of the solid phase. The solid phase mainly consisting of 1,2,4,5-tetraethylbenzene was subjected to the catalytic vapor-phase oxidation using Catalysts F and J of Example 1. The results are shown in Table 7.

TABLE 7

| Run No. | Purity and recovery of solid phase (%) | | Yield of pyromellitic dianhydride (mole %) | |
| --- | --- | --- | --- | --- |
| | Purity | Recovery | Catalyst F | Catalyst J |
| 1 | 86.1 | 45.1 | 59.0 | 60.1 |
| 2 | 91.0 | 41.2 | 64.0 | 65.2 |
| 3 | 75.8 | 60.1 | 53.1 | — |

What is claimed is:
1. A process for producing pyromellitic dianhydride, comprising:
(1) obtaining a polyethylbenzene fraction comprising di- and triethylbenzenes formed as a by-product in the manufacture of ethylbenzene;
(2) reacting the fraction with an ethylating agent in a reaction system containing a Friedel-Crafts catalyst or a solid acid catalyst until 3.0 to 5.0 moles of ethyl groups are introduced into 1 mole of benzene ring contained in the fraction;
(3) separating a tetraethylbenzene fraction from the reaction system by distillation, whereby a concentration of at least 90% tetraethylbenzene is obtained;
(4) cooling the concentrated tetraethylbenzenes to −10° to −30° C. to form crystals under a centrifugal force of 500 G or more to effect the separation of a solid phase having 1,2,4,5-tetraethylbenzene of a purity of 80–95% and a liquid phase having 1,2,3-tetraethylbenzene;
(5) oxidizing the 1,2,4,5-tetraethylbenzene to pyromellitic dianhydride in the vapor phase in the presence of a catalyst comprising vanadium pentoxide, titanium dioxide and an inert support;
(6) subjecting at least a portion of said liquid phase to an isomerization reaction system or the reaction system of step 2; and
(7) subjecting at least a portion of benzene derivatives other than the tetraethylbenzenes obtained in step 3 to the reaction system of step 2 or a transalkylation reaction system.

2. The process of claim 1, wherein said ethylating agent is ethylene.

3. The process of claim 1, wherein said solid acid catalyst is a zeolite.

4. The process of claim 1, wherein the polyethylbenzenes of step 2 are reacted until 3.5 to 4.8 moles of ethyl groups are introduced into 1 mole of benzene.

* * * * *